(12) United States Patent
Schoepp et al.

(10) Patent No.: US 11,540,742 B2
(45) Date of Patent: Jan. 3, 2023

(54) NAVIGATION SYSTEM FOR AND METHOD OF TRACKING THE POSITION OF A WORK TARGET

(71) Applicant: Stryker European Operations Holdings LLC, Kalamazoo, MI (US)

(72) Inventors: Hans Schoepp, Freiburg (DE); Jochen Breisacher, Teningen (DE); Juergen Kaltenbrunn, Loeffingen (DE)

(73) Assignee: Stryker European Operations Holdings LLC, Kalamazoo, MI (US)

(*) Notice: Subject to any disclaimer, the term of this patent is extended or adjusted under 35 U.S.C. 154(b) by 181 days.

(21) Appl. No.: 16/585,870

(22) Filed: Sep. 27, 2019

(65) Prior Publication Data

US 2020/0022615 A1  Jan. 23, 2020

Related U.S. Application Data

(63) Continuation of application No. 14/710,998, filed on May 13, 2015, now Pat. No. 10,575,756.

(30) Foreign Application Priority Data

May 14, 2014  (EP) .................................. 14001698

(51) Int. Cl.
*A61B 5/06* (2006.01)
*A61B 34/20* (2016.01)
(Continued)

(52) U.S. Cl.
CPC .............. *A61B 5/061* (2013.01); *A61B 34/20* (2016.02); *A61B 2017/00946* (2013.01);
(Continued)

(58) Field of Classification Search
None
See application file for complete search history.

(56) References Cited

U.S. PATENT DOCUMENTS

| 5,588,430 A | 12/1996 | Bova et al. |
| 5,622,170 A | 4/1997 | Schulz |

(Continued)

FOREIGN PATENT DOCUMENTS

| CN | 103230304 A | 8/2013 |
| WO | 9840026 A1 | 9/1998 |

(Continued)

OTHER PUBLICATIONS

Ben-Gal, "Outlier Detection." Data Mining and Knowledge Discovery Handbook: A Complete Guide for Practitioners and Researchers, 2005.

(Continued)

*Primary Examiner* — Yi-Shan Yang
(74) *Attorney, Agent, or Firm* — Howard & Howard Attorneys PLLC

(57) ABSTRACT

Navigation system and method for tracking movement of a patient during surgery. Image data is acquired by imaging the patient with a base layer of a skin-based patient tracking apparatus secured to the patient's skin. The skin-based patient tracking apparatus includes a plurality of optical surgical tracking elements. A computer processor arrangement is adapted to implement a navigation routine. The patient position is registered to the image data. The movement of the patient is tracked based on movement of the plurality of optical surgical tracking elements. The movement of the patient's skin is tracked by determining positions of the optical surgical tracking elements both before and after a deformation of the skin-based patient tracking apparatus. Movement of the patient's skin results in corresponding movement of the surgical tracking elements to provide a dynamic reference frame for use in continuously tracking movement of a patient's skin during surgery.

20 Claims, 7 Drawing Sheets

(51) Int. Cl.
*A61B 17/00* (2006.01)
*A61B 90/00* (2016.01)

(52) U.S. Cl.
CPC ............... *A61B 2034/2051* (2016.02); *A61B 2034/2055* (2016.02); *A61B 2034/2072* (2016.02); *A61B 2090/364* (2016.02); *A61B 2090/3983* (2016.02)

(56) References Cited

U.S. PATENT DOCUMENTS

| | | | |
|---|---|---|---|
| 5,772,594 | A | 6/1998 | Barrick |
| 5,817,105 | A | 10/1998 | Van Der Brug |
| 5,828,770 | A | 10/1998 | Leis et al. |
| 5,868,673 | A | 2/1999 | Vesely |
| 5,871,445 | A | 2/1999 | Bucholz |
| 5,902,239 | A | 5/1999 | Buurman |
| 5,954,648 | A | 9/1999 | Van Der Brug |
| 6,006,126 | A | 12/1999 | Cosman |
| 6,061,644 | A | 5/2000 | Leis |
| 6,127,672 | A | 10/2000 | Danisch |
| 6,146,390 | A | 11/2000 | Heilbrun et al. |
| 6,165,181 | A | 12/2000 | Heilbrun et al. |
| 6,216,029 | B1 | 4/2001 | Paltieli |
| 6,351,659 | B1 | 2/2002 | Vilsmeier |
| 6,405,072 | B1 | 6/2002 | Cosman |
| 6,412,491 | B1 | 7/2002 | Rusin |
| 6,442,416 | B1 | 8/2002 | Schultz |
| 6,675,040 | B1 | 1/2004 | Cosman |
| 6,694,167 | B1 | 2/2004 | Ferre et al. |
| 7,169,155 | B2 | 1/2007 | Chu et al. |
| 7,734,328 | B2 | 6/2010 | Vaillant et al. |
| 7,747,312 | B2 | 6/2010 | Barrick et al. |
| 7,751,868 | B2 | 7/2010 | Glossop |
| 7,869,861 | B2 | 1/2011 | Moctezuma de la Barrera et al. |
| 8,108,025 | B2 | 1/2012 | Csavoy et al. |
| 8,195,272 | B2 | 6/2012 | Piferi et al. |
| 8,204,575 | B2 | 6/2012 | Stetz et al. |
| 8,363,259 | B2 | 1/2013 | Gilboa |
| 8,374,678 | B2 | 2/2013 | Graumann |
| 8,457,719 | B2 | 6/2013 | Moctezuma de la Barrera et al. |
| 8,483,434 | B2 | 7/2013 | Buehner et al. |
| 8,620,405 | B2 | 12/2013 | McClelland et al. |
| 8,644,906 | B2 | 2/2014 | Piferi et al. |
| 8,657,809 | B2 | 2/2014 | Schoepp |
| 9,202,387 | B2 | 12/2015 | Gilboa |
| 2002/0087101 | A1 | 7/2002 | Barrick et al. |
| 2005/0215879 | A1 | 9/2005 | Chuanggui |
| 2005/0249426 | A1 | 11/2005 | Badawy |
| 2006/0058604 | A1 | 3/2006 | Avinash et al. |
| 2006/0293557 | A1 | 12/2006 | Chuanggui et al. |
| 2007/0219443 | A1 | 9/2007 | Ehnholm et al. |
| 2007/0236514 | A1 | 10/2007 | Agusanto et al. |
| 2008/0201016 | A1 | 8/2008 | Finlay |
| 2008/0269602 | A1* | 10/2008 | Csavoy .................. A61B 34/20 600/426 |
| 2010/0076306 | A1 | 3/2010 | Daigneault et al. |
| 2010/0081919 | A1 | 4/2010 | Hyde et al. |
| 2010/0298695 | A1 | 11/2010 | Wenger |
| 2010/0305427 | A1 | 12/2010 | Huber et al. |
| 2011/0054303 | A1 | 3/2011 | Barrick et al. |
| 2011/0077510 | A1 | 3/2011 | Moctezuma de la Barrera et al. |
| 2011/0263971 | A1 | 10/2011 | Nikou et al. |
| 2011/0268248 | A1 | 11/2011 | Simon et al. |
| 2011/0270084 | A1 | 11/2011 | Choi et al. |
| 2011/0295110 | A1 | 12/2011 | Manzke et al. |
| 2011/0306873 | A1 | 12/2011 | Shenai et al. |
| 2012/0071753 | A1 | 3/2012 | Hunter et al. |
| 2012/0109150 | A1 | 5/2012 | Quaid et al. |
| 2012/0179027 | A1 | 7/2012 | Suthanthiran et al. |
| 2012/0232377 | A1 | 9/2012 | Nottmeier |
| 2013/0189663 | A1* | 7/2013 | Tuchschmid .......... G09B 23/28 434/262 |
| 2013/0217998 | A1 | 8/2013 | Mahfouz et al. |
| 2013/0345718 | A1 | 12/2013 | Crawford et al. |
| 2014/0088410 | A1 | 3/2014 | Wu |
| 2015/0051489 | A1 | 2/2015 | Caluser et al. |
| 2015/0190205 | A1* | 7/2015 | Grass ..................... A61B 5/065 600/408 |
| 2015/0304634 | A1 | 10/2015 | Karvounis |
| 2015/0327948 | A1 | 11/2015 | Schoepp et al. |
| 2016/0029997 | A1 | 2/2016 | Moctezuma de la Barrera et al. |
| 2016/0278865 | A1 | 9/2016 | Capote et al. |

FOREIGN PATENT DOCUMENTS

| | | |
|---|---|---|
| WO | 2012052929 A3 | 6/2012 |
| WO | 2013119801 A2 | 8/2013 |

OTHER PUBLICATIONS

English language abstract and machine-assisted English translation for CN 103230304 extracted from espacenet.com database on Jun. 12, 2019, 11 pages.

European Search Report for Application EP14001698.1 dated Dec. 18, 2014; 4 pages.

* cited by examiner

NAVIGATION SYSTEM FOR AND METHOD OF TRACKING THE POSITION OF A WORK TARGET

CROSS REFERENCE TO RELATED APPLICATIONS

This application is a continuation of copending U.S. patent application Ser. No. 14/710,998, filed May 13, 2015, which claims priority to European Patent Application No. 14001698.1, filed May 14, 2014, the entire contents of each are hereby incorporated by reference.

TECHNICAL FIELD

The present disclosure is directed toward a navigation system for tracking the position of a work target with a trackable device, such as a surgical navigation system. The disclosure is also directed toward a method of tracking the position of the work target using such a navigation system.

BACKGROUND

Navigation systems for tracking the position of one or more work targets located inside a body, either alone or in relation to one or more various working tools, are used in many types of applications. One application in which navigation systems are commonly used is in the field of navigated surgical procedures. In this field, surgical navigation systems are now commonly used to assist in planning a surgical procedure or executing a planned surgical procedure, so as to improve the accuracy of the surgical procedure and minimize the invasiveness thereof.

In some surgical navigation systems, a rigid trackable device is secured to the patient so as to be fixed in relation to some portion of the patient's body. A computer implemented tracking system is used to track the position of the trackable device and, based on a previously determined spatial relationship between the trackable device and some area of interest within the patient, thereby track the position of a work target within the patient. The computer-implemented tracking system is also used to track the position of a surgical working tool, for example by means of a second trackable device secured to the working tool. From these two tracked positions, the navigation system thereby is able to track the position of the working tool relative to the working target within the patient. The tracking information is then correlated with previously defined surgical plan information relative to one or more intra- or preoperative scan information data sets, such as CT (computer tomography) images, MRI (magnetic resonance imaging) images, X-ray images, ultrasound image data, or other similar information about the body of the patient, by one or more methods of registering the pre-operative scan information data to the intra-operative tracking information.

A limiting design parameter of such a navigation system is that the trackable device usually must be invasively attached to the patient, such as with pins or other fasteners securely fastened to a bone. Such securement can lead to additional possibilities for potential problems with post-surgical recovery of the patient. Additionally, the various navigational routines implemented by the computer-implemented tracking system are based on the assumption that the trackable device does not move relative to the patient and the target area during a navigation procedure. Therefore, movement of the trackable device relative to the patient during a navigation process, such as by accidental bumping, loss of fixation, or other means, can lead to excessive errors and require a complete re-setting or reconfiguration of the navigation system, which can use up valuable time during a surgical procedure.

Other surgical navigation systems use a trackable device formed of a flexible substrate with several LEDs (Light Emitting Diodes) carried by the flexible substrate. The flexible substrate is secured to the skin of the patient in a manner and location to prevent or minimize deformation or movement relative to the features of the patient. Thus, the trackable device is generally attached to very bony areas of the patient, such as the skull and/or nose portions so as to remain in a fixed position relative to a work target inside the patient once a navigation procedure has begun. A limitation with such a navigation system, however, is that any deformation of the trackable device once a navigation procedure has been started can lead to excessive navigation errors and or require reconfiguration of the navigation system.

SUMMARY

According to some aspects, a navigation system for and method of tracking the position of the work target is provided, wherein the navigation system can detect distortions of a trackable device during the navigation procedure. In some circumstances, the navigation system can compensate for such distortions in a way that reduces or eliminates navigational error and/or avoids or reduces the need to re-set the navigation system during the navigation procedure.

According to some aspects, a navigation system for tracking the position of a work target located inside a body that is compressible and has a distortable outer surface is provided. The navigation system includes a trackable device and a computer-implemented tracking system. The trackable device includes a plurality of tracking points configured to be secured to the outer surface of the body. The tracking points are configured to be moveable relative to each other when secured to the outer surface of the body. The computer-implemented tracking system is adapted to remotely track the positions of each tracking point relative to a coordinate system. The tracking system includes a computer processor arrangement adapted to implement a navigation routine that includes the steps: accessing an initial model of the trackable device, the initial model having an initial shape based on initial locations of a set of the tracking points; registering the initial model with an initial position of the work target in an image of the work target; sensing a deformation of the trackable device with the tracking system after registering the initial model; creating a refined model of the trackable device that compensates for the deformation; and calculating the current position of the work target from the refined model.

According to some aspects, a method of tracking the position of a work target located inside a body with a navigation system includes the steps: accessing an initial model of the trackable device, the initial model having an initial shape based on initial locations of a set of the tracking points; registering the initial model with an initial position of the work target in an image of the work target; sensing a deformation of the trackable device with the tracking system after registering the initial model; creating a refined model of the trackable device that compensates for the deformations; and calculating the current position of the work target from the refined model. The method may be implemented by a computer-implemented tracking system, such as with hardware and/or software, configured to remotely track the positions of tracking points of a trackable device relative to a coordinate system. The method may be implemented with the use of a trackable device having a plurality of tracking points configured to be secured to the outer surface of the body, wherein the tracking points are configured to be moveable relative to each other when secured to the outer surface of the body.

These and other aspects may include any one or more of the various optional arrangements and features described herein.

In some arrangements, the steps of accessing and registering may be performed only one time during a navigation procedure, such as at or near the beginning of the procedure. The steps of sensing a deformation, creating a refined model, and calculating the position of the work target may be performed one or more times, such as iteratively, during the course of a navigation procedure.

In some arrangements, the step of creating a refined model may include removing one or more of the sensed tracking points of the set and/or adjusting a sensed location of a tracking point relative to sensed locations of the other tracking points in the set. For example, the step of creating a refined model may include removing at least one of the tracking points of the set that is deformed more than a deviation threshold from the initial shape or any other reference. Also by way of example, the step of creating a refined model may include adjusting a sensed location of a tracking point relative to sensed locations of the other tracking points in the set as a function of a spatial deviation between the sensed location of the tracking point and the initial location of the tracking point and/or optionally relative to the initial locations of one or more of the other tracking points.

In some arrangements, sensing the deformation may include tracking subsequent locations of the tracking points of the set after the initial model is registered, the subsequent locations defining a deformed shape. A deformed model of the trackable device may be based on the sensed locations of the tracking points and the deformed shape. Then the deformation of the trackable device may be identified based on a difference between the deformed shape and the initial shape.

In some arrangements, the step of identifying the deformation includes matching the initial shape to the deformed shape and calculating a spatial deviation of a tracking point of the set. Optionally the matching may be performed by transforming the initial locations of the tracking points to the subsequent locations of the tracking points and comparing the same points in the two models to each other to identify the spatial deviation. For example, initial coordinates of the tracking points (e.g., the initial shape) may be transformed to attempt to match measured coordinates in a point cloud of sensed tracking points (e.g., the deformed shape). This transformation may be an orthogonal transformation. Such a transformation and matching may include a least squares matching algorithm to find a best-fit comparison. The matched shapes may then be compared to calculate spatial deviations of the points, such as the absolute value of the distance between the coordinates of one or more of the measured tracking points and the transformed coordinates of the initial locations of the same tracking point. Alternatively or additionally, the coordinates of the sensed tracking points may be transformed and matched to the coordinates of the initial locations of the same tracking points, or other coordinate transformations suitable for matching and comparing the initial and deformed shape may be used.

In some arrangements, the step of creating a refined model includes excluding the sensed tracking point from the set when the spatial deviation for that tracking point exceeds a defined spatial deviation threshold and/or has a spatial deviation more than at least one other sensed tracking point in the set. Optionally, the tracking point is excluded only when its spatial deviation exceeds the defined spatial deviation threshold and has the largest spatial deviation of all the tracking points in the set, whereby only one (e.g., the most deformed) tracking point is excluded at a time. The sensed tracking point may be excluded by removing it from the set of tracking points used to form the refined model. Thus, the refined model may be based on a reduced set of the sensed tracking points (relative to the initial model and/or the deformed model) without the subsequent location of the removed tracking point. Optionally, the deformed tracking point may be removed from the set of sensed tracking points without modifying the shape of remaining portions of the deformed model.

In some arrangements, the step of creating a refined model includes adjusting the position of a sensed tracking point when it is identified as being deformed. The location of the deformed tracking point in the deformed model may be adjusted into a corrected position in the refined model. The corrected position of the deformed tracking point may thus be retained in the refined model rather than omitting the deformed tracking from refined model. The sensed location of a tracking point may be adjusted relative to the sensed locations of the other tracking points in the set as a function of the relative positions of the tracking points to each other and the spatial deviations of these relative positions and/or relative distances. The adjusting may be performed based on a force spring model assumption of movements of the skin of a patient in a finite element method (FEM) analysis. The spatial deviation of a deformed tracking point may be equated to a resultant force. A set of forces applied to the force spring model may be calculated to shift the deformed tracking point toward the original position in the original model. The resultant shifting of one or more of the remaining tracking points may also be modeled. One or more of the sensed tracking points may be held to maintain a fixed position relative to the work target, while other ones of the sensed tracking points are shifted based on the force spring model in the FEM analysis.

The deviation threshold may be a predefined static value and/or be a dynamic value dependent on selectable factors. Optionally, the deviation threshold can be based on a comparison of the spatial deviation for the tracking point relative to an averaged spatial deviation for up to all of the tracking points in the set. An averaged spatial deviation may include a direct average, a weighted average, and/or another type of average. A tracking point may be called and/or considered a deformed tracking point and/or considered to have an unacceptable location error when its spatial deviation exceeds such a deviation threshold and/or exceeds the spatial deviation of other ones of the tracking points, for example, by having the largest spatial deviation of all the tracking points. The decision of whether to remove and/or adjust the sensed location of a tracking point in the refined model may depend upon whether the tracking point is considered to be a deformed tracking point and/or have an unacceptable location error.

In some arrangements, before the current position of the work target is calculated, the steps of matching the initial shape to the deformed shape, calculating a spatial deviation, and removing a tracking point are iteratively repeated. In subsequent iterations, the matching is performed with a reduced number of tracking points due to the exclusion of the previously removed tracking point. These steps may be iteratively repeated until at least no further sensed tracking points are removed from the set of tracking points and/or the set of sensed tracking points includes fewer than a pre-defined minimum number of tracking points. The pre-defined minimum number of tracking points may be a statically defined number or may be a dynamically defined number, for example based on a function of parameters obtained during the navigation procedure. Optionally, the navigation routine provides a notification to a user if and when the set of tracking points included in the refined model includes fewer than the pre-defined minimum number of tracking points. Such a notification may include providing an audible or visible notification, such a warning, and/or automatically terminating or suspending the navigation routine.

The navigation routine may be adapted to provide a notification to a user in when one or more error thresholds are met or exceeded. In some arrangements, the navigation routine estimates an expected error of the current position of the work target calculated from the initial model and the deformation of the trackable device and/or the reduction of tracking points in the refined model. In some arrangements, the navigation routine calculates an averaged spatial deviation of some or all the tracking points in the set of tracking points from the spatial deviations. Optionally, the navigation routine may provide an indication to a user when the expected error exceeds a pre-defined maximum error threshold for the work target and/or the averaged spatial deviation exceeds a pre-defined maximum error threshold. The pre-defined error thresholds may be statically defined numbers and/or may be a dynamically defined numbers, for example based on a function of parameters obtained during the navigation procedure. The indication may include a warning message and/or ending the navigation routine, such as by terminating or suspending the navigation routine. The warning message may include a visual message, such as with a visual warning provided on a display screen, an audible message, such as with an audible alert provided via a speaker, and/or another type of message that is designed to attract the attention of the user.

In some arrangements, the navigation routine senses the initial locations of the tracking points of the set of tracking points and/or may import the initial locations from some other source, such as a memory or database. The sensing may be performed with a navigation sensor configured to measure a position of the tracking points relative to the navigation sensor. Such a navigation sensor may, for example, include one or more cameras and/or a magnetic position sensor, although other types of electronic navigation sensors could also or alternatively be used. The sensing may be performed by detecting with and/or extraction from a pre- or intraoperative scan image, such as a CT scan, MRI, X-ray, ultrasound, optical, or other similar imaging modality. The navigation routine may create the initial model of the trackable device from the initial locations of the set of tracking points, or the model may be imported from some other source, such as a memory or database.

Registration of the initial model of the trackable device with an initial position of the work target in an image of the work target may be performed in any suitable manner. In some arrangements, the step of registration includes identifying an initial pose (i.e., a position and orientation of a three-dimensional shape relative to a three-dimensional coordinate system) of the initial model relative to a global coordinate system from the initial locations of the set of tracking points, and registering the initial pose of the initial model to the initial position of the work target in an image of the work target, such as an MRI, CT, X-ray, ultrasound, optical, or other similar imaging modality, relative to the global coordinate system. Suitable registration methods that may be used, include surface matching techniques and point-to-point matching techniques. The navigation routine may include an automatic registration feature, such as a shape matching routine or any known automatic registration routine, and/or may include a manual registration feature, such as by a point-to-point registration routine or any known manual registration routine. However, any suitable registration procedure may be used.

The trackable device may include a flexible substrate configured to be secured to the outer surface of the body, however, a rigid trackable device could also be used. One or more of the tracking points may be carried by the same flexible substrate or by separate flexible substrates. The flexible substrate may have almost any shape, such as a sheet having a relatively thin thickness with opposite first and second sides and one or more peripheral edges. The flexible substrate may have complete flexibility in all directions, limited flexibility in only some directions, and/or have regions of complete flexibility and regions of limited flexibility. In some arrangements, the flexible substrate may be in the shape of a frame surrounding a window through a central portion of the trackable device. The frame may have the shape of any closed or semi-closed shape, such as a rectangle, a square, a circle, an oval, a U, a semi-circle, or an H. The window may be sized and shaped to allow the frame to partially or completely surround a surgical area on the patient's skin over the work target. The window may be sized and shaped to provide a sufficient space through which a surgical procedure on the work target can be performed. Optionally, the number of tracking points on the flexible substrate may be between twenty and forty optical emitters disposed on the flexible substrate and extending around the window. However, more or fewer tracking points may also be used. In some arrangements, the trackable device includes two or more flexible substrates configured to be secured separately to the outer surface of the body, for example by being spaced apart from each other. Each of the substrates may carry only one, or may carry more than one tracking point, for example between 2 and 20. Each flexible substrate may be in the form of a patch and may have almost any shape, such as rectangular, circular, oval, and so forth. The flexible substrates may have other shapes, such as an elongate strip, cross, or star. In this manner, an array of separate flexible substrates may be located individually on the skin of a patient in the area around a work target in almost any shape or configuration desired. The tracking point or points may be disposed on one side of the flexible substrate. An adhesive may be disposed on the other side of the flexible substrate to allow the substrate to be secured to the outer surface of the body. The adhesive may be a bio-compatible adhesive suitable for securing the substrate to the skin of a patient without injuring the patient and allowing the substrate to be subsequently safely removed from the skin. The trackable device may be applied to the surface of the body, such as the skin of the patient, such that the centroid of the sensed of tracking points, that is, the centroid of the sensed point cloud, is very close to the working target that is to be tracked.

The tracking points may be any feature or structure adapted to be sensed by the computer-implemented tracking system. In some arrangements, the tracking points include an LED, a reflective surface, a reflective pattern, a magnetic coil, and/or an optically identifiable geometric shape that uniquely defines position and orientation.

A work piece may be adapted to be tracked by the tracking system, wherein the tracking system is adapted to track the position of the work piece relative to the coordinate system. The navigation routine further include the step of calculating the position of the work piece relative to the position of the work target based on the tracked position of the work piece and the calculated position of the work target.

In some arrangements, the trackable device includes a data communication link suitable for sending and/or receiving data to and from the computer-implemented tracking system. The optical emitters may be selectively activated in response to command signals received from the tracking system through the data communication link. Information regarding physical constraints of how the tracking points can move relative to each other, including at least one of flexibility of the substrate, rigidity of the substrate, and type of connection between tracking points may be associated with the trackable device. The information regarding physical constraints may be communicated to the computer-implemented tracking system by the data communication link, and/or the information may already be stored on the computer system.

In some arrangements, the navigation system includes a computer processor in data communication with one or more tracking sensors. The data connection may be wired and/or wireless. The navigation routine may be implemented by hardware and/or software accessed by or installed on the computer processor directly or run remotely, such as via an internet connection to one or more other computer processors. The navigation routine may be stored in one or more non-transient computer memory, such as RAM or ROM. Additional data, such as scan image data, procedure planning data, user preferences, patient data, and other useful data may be stored, for example, in an electronic database also provided in non-transient computer memory. The computer processor may have access to the navigation routine and/or the database so as to be able to implement the methods and processes described herein. Input/output devices, such as a keyboard, mouse, display monitor, may be operatively connected with the computer processor to facilitate ease of use by a user. The navigation system may have a data connection that allows for remote access and/or control, for example via an internet, local area network, wide area network, or similar data connection. Other common computer hardware and/or software helpful, necessary, and/or suitable for implementing computerized, planning, control, and/or execution of a navigation procedure may be included as part of the navigation system in a manner well understood in the art.

In some arrangements, the navigation system is a surgical navigation system adapted for use in a surgical operating theater to help navigate a surgeon through a surgical procedure. The trackable device may be adapted to be attached to the skin of a surgical patient and to extend around a surgical area on the patient without covering the surgical area. The surgical area may include one or more of a bone and an organ, such as the spine, a lung, the liver, a femur, and the pelvis. However, the work target may include other bones, organs, and/or items disposed in, on, or near the body.

The computer-implemented tracking system may include sensors for sensing the tracking points in the form or one or more cameras. In some arrangements, the computer-implemented tracking system may include a plurality of cameras. Each camera may be adapted to capture a view of the tracking points, and the computer processor arrangement may be adapted to calculate the location of each tracking point relative to the coordinate system by triangulation of the views of the tracking points. The cameras may be supported independently of the body, a working tool, and/or a user. In some arrangements, the cameras are carried by a frame that is adapted to be secured to, for example, a wall, a support trolley, or other structure. In some arrangements, one or more cameras may be carried by a surgical tool, and the computer processor arrangement may be adapted to calculate a pose of the tool relative to the work target based on images of the trackable device captured by the one or more cameras. In some arrangements, one or more of the tracking points may include an optical target that uniquely defines a pose. The computer-implemented tracking system may include a camera adapted to capture an image of the optical target, and the computer processor arrangement may be adapted to implement a tracking routine that calculates the pose of the optical target from the captured image.

BRIEF DESCRIPTION OF THE DRAWINGS

The above and other aspects and features of the navigation system and method presented herein may be understood further with reference to the following description and drawings of exemplary arrangements.

DETAILED DESCRIPTION

Figure 1:
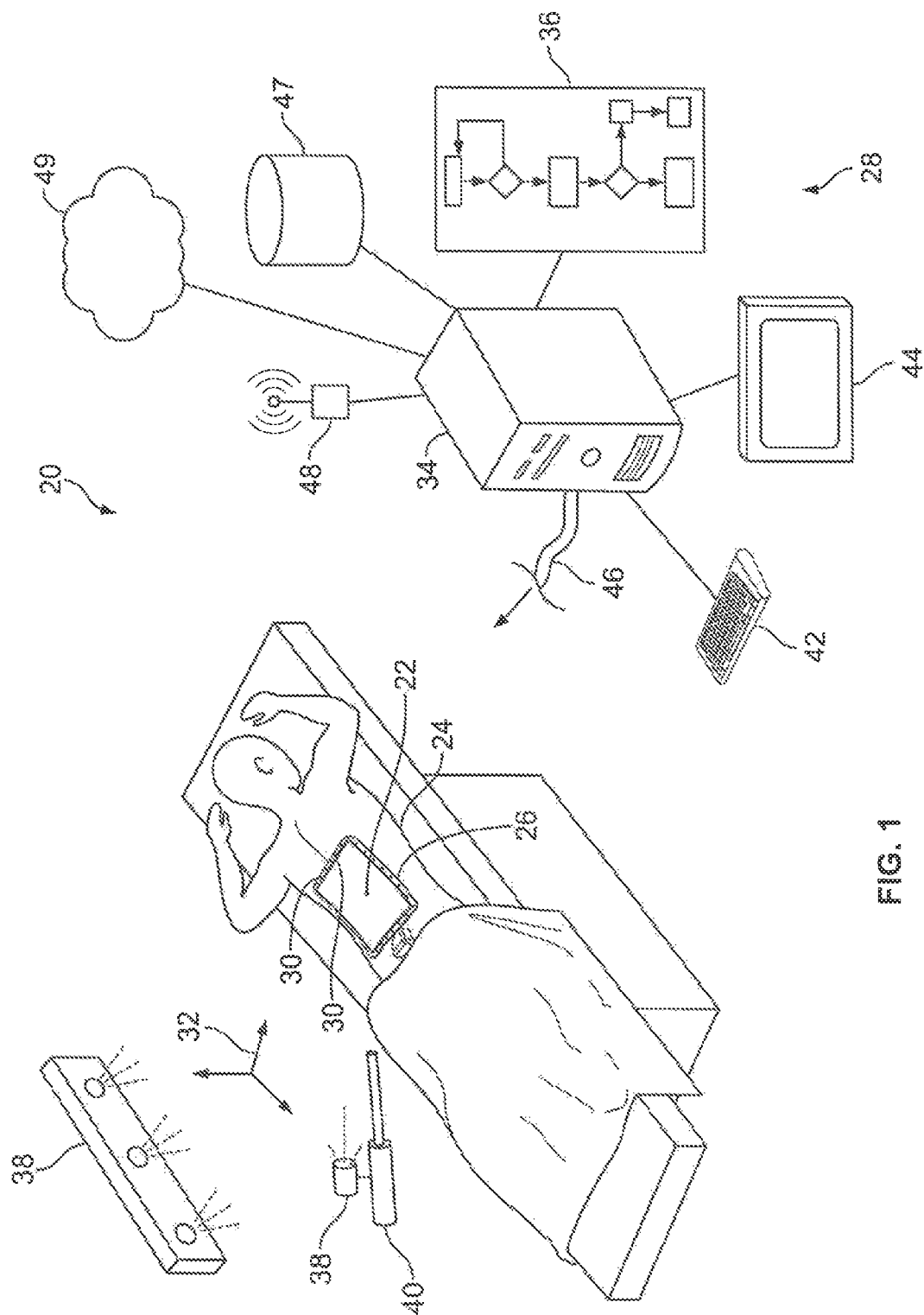
FIG. 1 is a schematic diagram of a navigation system according to an exemplary arrangement of the present disclosure.
Figure 2:
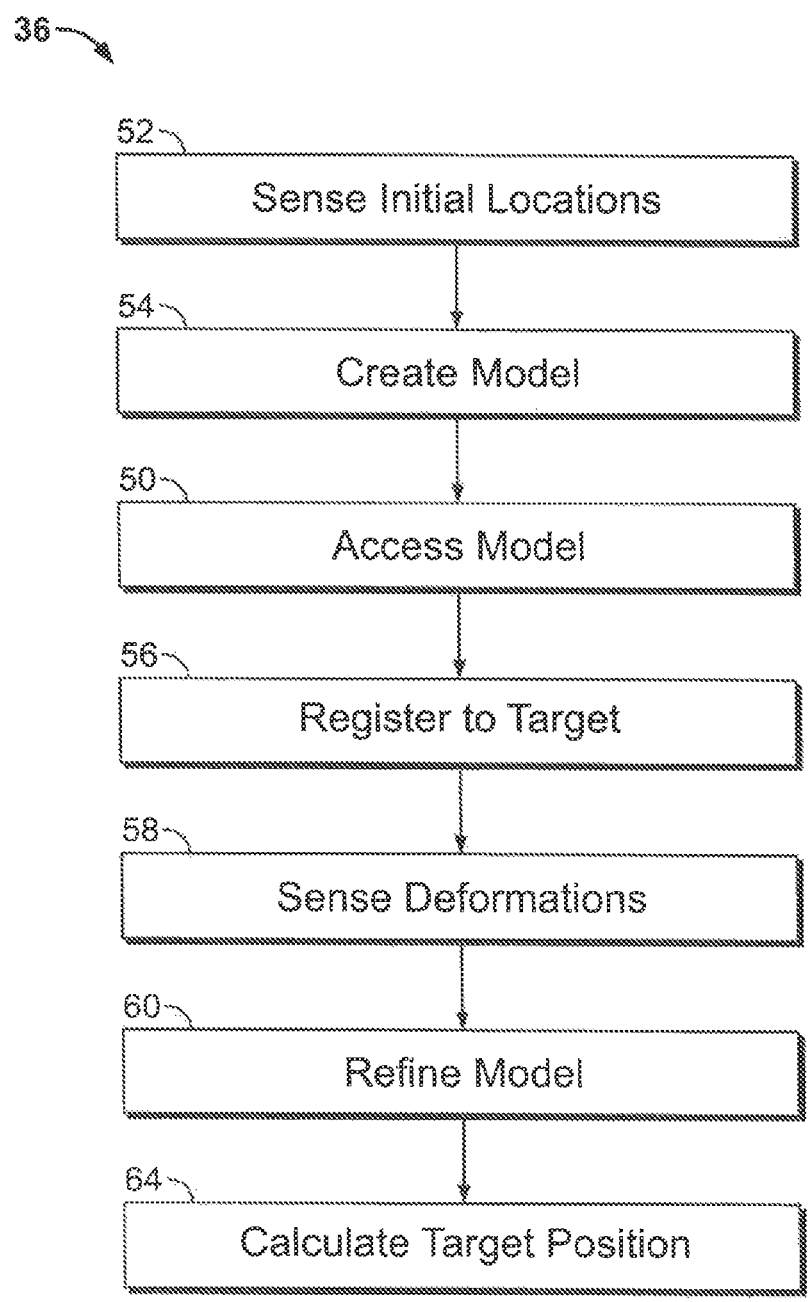
FIG. 2 is a logic flow diagram of a navigation routine implemented by the navigation system of FIG. 1 according to an exemplary method.

Turning now to FIGS. 1 and 2, a navigation system 20 is arranged for tracking the position of a work target 22 located near a body 24. The work target 22 may be located inside the body 24, on the outer surface of the body 24, and/or even spaced from the body 24. The navigation system 20 includes a trackable device 26 that is adapted to be secured on the exterior of the body 24, and a computer implemented tracking system 28 which is adapted to track the position of the trackable device 26 during a navigation procedure and to detect and compensate for some deformations of the trackable device 26 during a navigation procedure. The navigation system 20 is particularly well suited for tracking the position of the work target 22 wherein the body 24 is compressible and/or has a distortable outer surface. However, the navigation system 20 is suitable for use with a body 24 that has any shape and figuration, including having a fixed shape. In the depicted example, the navigation system 20 is a surgical navigation system adapted and arranged for tracking the position of a work target inside of a patient's body, and preferably relative to one or more working tools, such as at 40, and/or operative plans. In the depicted example, the navigation system 20 is particularly adapted for surgical navigation on a human. However, the navigation system 20 may be used for surgery on other animals, and/or may be adapted for tracking the position of the work target in other types of bodies that are not humans or animals. The surgical navigation system 20 is adapted to track the position of a bone and/or an organ disposed inside of the patient 24. Thus, the work target 22 may include bones of a spine, a lung, a liver, a femur, a pelvis, an orthopedic implant, or any other object disposed inside the body. However, the navigation system 20 may also be used to track the position of work targets disposed outside of the body, such as on the skin of the patient 24. In the description of this particular exemplary arrangement, the work target 22 may be a vertebrae or a portion of the patient's spine, it being understood that other work targets are also contemplated.

The trackable device 26 includes a plurality of tracking points 30 that are configured to be secured to the outer surface of the body 24, such as the outer surface of the skin of a patient. The tracking points 30 are moveable relative to each other, such as by deforming relative to each other, when secured to the skin of the patient. The trackable device 26 is not limited to a particular shape or form, and may be rigid, flexible, and/or have multiple separate sections. Some exemplary shapes and forms of the trackable device 26 suitable for use in the navigation system 20 are discussed in detail hereinafter with reference to the trackable devices 26a-d shown in FIGS. 8 to 11. For purposes of example only, the trackable device 26 in FIG. 1 has a plurality of tracking points 30, such as LED's, disposed on a flexible substrate having the shape of a generally rectangular frame with an open window there through that can be removably secured to the patient's skin with adhesive, generally similar to the trackable device 26a shown and described hereinafter with respect to FIG. 8. However, the tracking device 26 is not limited to this particular arrangement.

The computer-implemented tracking system 28 is adapted to remotely track the position of one or more of the tracking points 30 relative to a coordinate system 32. The coordinate system 32 may be any coordinate system suitable for use with the tracking system 28, such as a global coordinate system, a local coordinate system relative to the patient 24, and/or a local coordinate system relative to some portion of the tracking system 28, such as the working tool 40 or the trackable device 26. The tracking system 28 includes a computer processor arrangement 34 adapted to implement a navigation routine 36 that is capable of detecting deformations of the trackable device 26 and compensating for at least some detected deformations during a navigation procedure implemented with the navigation system 20, as described in further detail hereinafter.

The computer-implemented tracking system 28 may take a variety of different forms, wherein a computer processor arrangement preferably is adapted to receive data from one or more sensors 38 relative to the locations of the tracking points 30, track the positions of the tracking points 30 relative to at least one coordinate system, and correlate the tracked positions to the positions of one or more additional features, such as a portion of the patient 24, the work tool 40, and/or virtual work plan information, such as a proposed osteotomy, suture, and the like. In the exemplary form shown in FIG. 1, the tracking system 28 includes the computer processor arrangement 34 and one or more sensors 38 adapted to sense the positions of the tracking points 30 remotely. The sensors 38 may include cameras, such as CCD cameras, CMOS cameras, and/or optical image cameras, magnetic sensors, radio frequency sensors, or any other sensor adapted to sufficiently sense the position of the tracking points 30. In the present exemplary arrangement, the sensors are in the form of cameras, which may be, for example, carried by a stand, secured to a wall of an operating room, and/or may be secured to the working tool 40 in a manner well understood in the art. However, other arrangements of the sensors 38 are also possible. Each of the cameras 38 is adapted to capture a view of the tracking points 30 from a different position, and the computer processor arrangement 34 includes software and/or hardware having computing instructions adapted to calculate the location of each tracking point 30 relative to the coordinate system 32 by triangulation of the different views of the same tracking points. Optionally, one or more cameras may be carried by the surgical tool 40, and the computer processor arrangement 34 may include computing instructions adapted to calculate the pose of a tool 40 relative to a pose of the work target 22 based on images of the trackable device 26 and/or the tracking points 30 captured by the one or more cameras 38 on the tool 40. The computer processor arrangement 34 includes hardware and/or software arrangement to implement the various routines and/or methods disclosed herein. In the exemplary arrangement of FIG. 1, the computer processor arrangement also includes input output/devices, such as a keyboard 42 and a display monitor 44, and one or more data communication devices, such as data communication cables 46 and/or wireless communication devices 48. The computer processor arrangement 34 further has access to one or more databases 47 for storing various data. Optionally, the computer processor arrangement includes a data connection to a larger computer network 49 such as via the internet, wide area network, local area network, or other computer networking means. Additional and/or alternative and/or fewer hardware and programming components may also be implemented as part of the computer processor arrangement 34 as would be understood in the art.

As illustrated in FIG. 2, the navigation routine 36 implements a plurality of method steps that, when suitably implemented together with other components of the navigation system 20, enable the navigation system to track the position of the work target 22, and optionally additional components such as the tool 40, relative to at least one coordinate system. The navigation routine 36 may be implemented in software programming code accessed and/or implemented by the computer processor 34, for example from the database 47 and/or from a remote source such as via the internet at 49, and/or may include one or more ASIC configurations, in a manner that would be understood in the computer programming and control arts.

Figure 3:
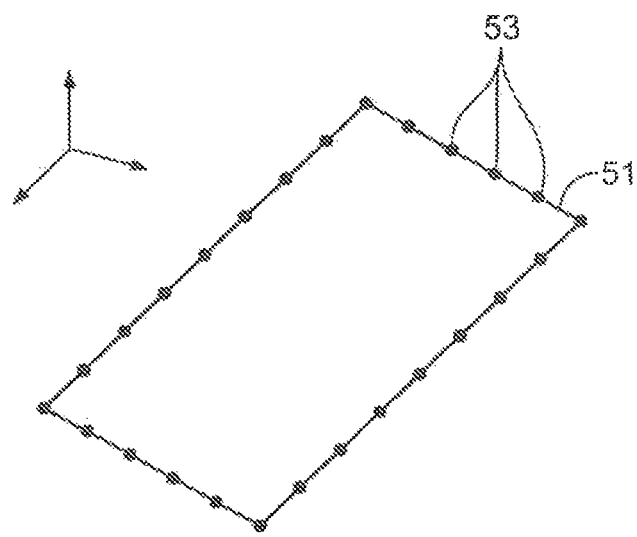
FIG. 3 is a schematic representation of an initial model of an exemplary trackable device in in the navigation system of FIG. 1.

A block 50 accesses an initial model of the trackable device, such as the model 51 shown schematically in FIG. 3. The initial model 51 defines an initial shape based on the initial locations 53 of a set of the tracking points 30 from the trackable device 26 after it has been secured to the skin of the patient. The initial model 51 may be formed separately from the navigation routine 36 or it may optionally be obtained and/or formed as part of the navigation routine 36. If formed separately from the navigation routine 36, the initial model 51 may for example be stored in the database 47 or accessed via a data communication connection from a remote source such as at 49.

In one optional arrangement where the initial model 51 is formed as part of the navigation routine 36, a block 52 obtains the initial locations 53 of the tracking points 30 after the trackable device 26 has been secured to the patient 24, and a block 54 creates the initial model 51 of the trackable device 26 from the initial locations 53 of the tracking points 30. The initial locations 53 may be in the form of coordinates relative to the coordinate system 32 or some other arbitrary coordinate system, for example, defined relative to the trackable device 26. In some arrangements, the initial locations 53 are obtained with one or more of the navigation sensors 38. In some arrangements, the initial locations 53 are obtained from image data, such as a pre-operative scan. For example, the trackable device 26 and the patient 24 may be scanned together after the trackable device 26 is attached to the patient 24. The initial model 51 is created based on the coordinates of the initial locations 53 of the tracking points 30, and may be the point cloud defined by the coordinates of the initial locations 53. However, other modeling techniques for creating the initial model 51 may be used. For example, a surface mesh may be generated based on the point cloud and apriori knowledge of the trackable device 26. In some arrangements the navigation routine 36 may create the initial model 51 of the trackable device at block 54 from the locations of the set of tracking points 30 obtained from a scan data set, such as a preoperative or intraoperative MRI, x-ray, or other type of scan, without obtaining the initial locations 53 with the sensors 38 at block 52.

Figure 4:
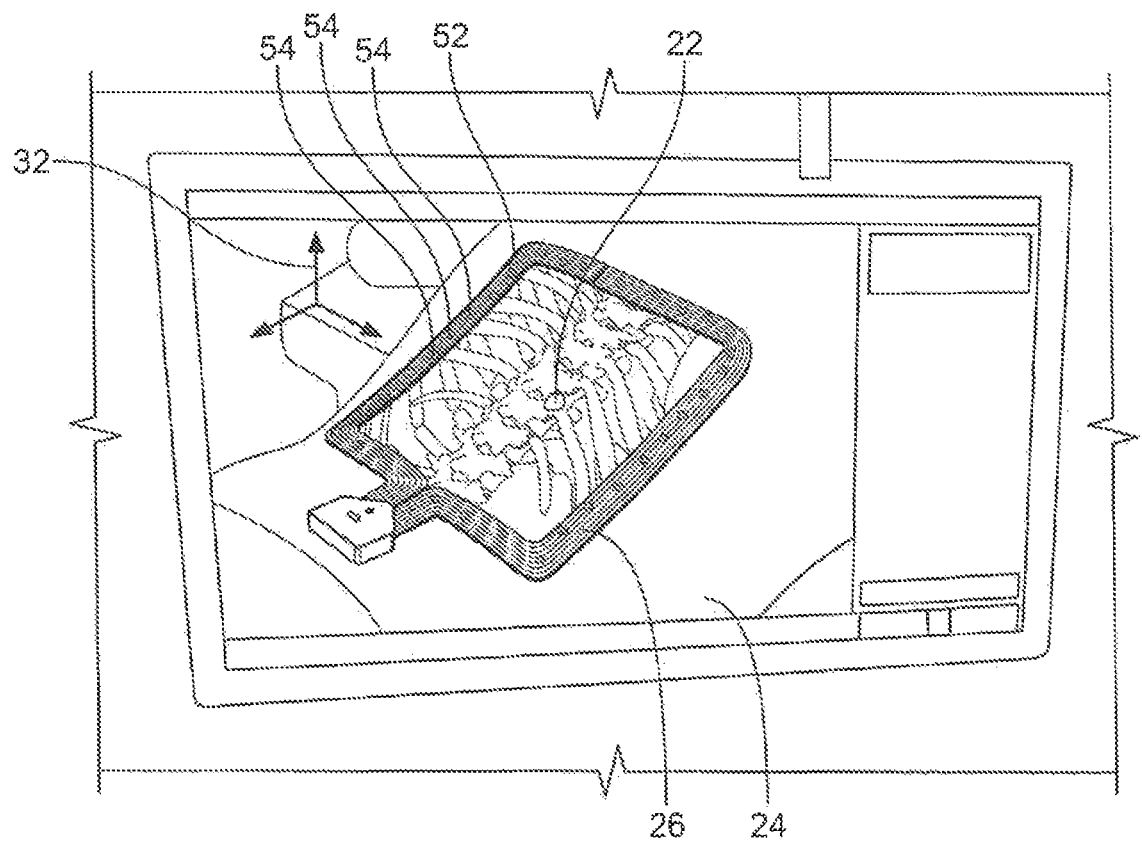
FIG. 4 is a schematic representation of registering the initial model of FIG. 3 with image data of the work target.

A block 56 registers the pose of the initial model 51 with an initial position of the work target 22 in an image data set, such as a pre-operative scan image of the patient, as shown schematically in FIG. 4. The step of registering may be performed in any manner understood in the art, such as with a point cloud matching technique, a point to point registration technique, and/or any other technique sufficient to register the pose of the initial model 51 as secured to the patient to the initial position of the work target 22 in image data set of the patient. In one arrangement, the registration may include identifying an initial pose of the initial model 51 relative to the coordinate system 32, such as a global coordinate system, from the initial locations 53 of the set of tracking points 30. Thereafter, the initial pose of the initial model 51 is registered to the initial pose of the work target 22 in a pre- or intra-operative scan image of the patient, such as an MRI, CT, X-ray, ultrasound, optical image, and the like.

Figure 5:
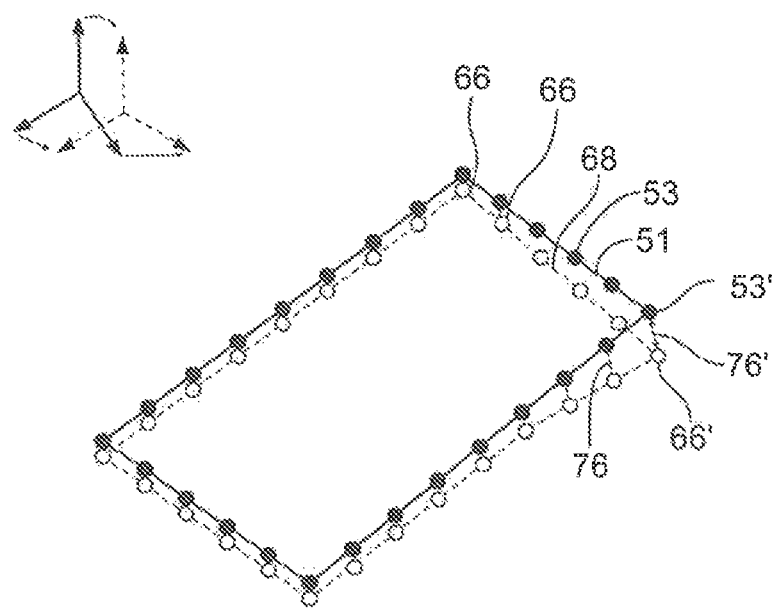
FIG. 5 is a schematic representation of sensing deformations of the trackable device in FIG. 1.

After registering, a block 58 senses deformation of the trackable device 26 while tracking the locations of the tracking points 30 during a navigation procedure, as depicted schematically in FIG. 5 and discussed in further detail hereinafter. For example, as seen in FIG. 5, the sensed locations 66' of the tracking points 30 in the upper right corner of the trackable device 26 have been deformed downwardly substantially from initial locations 53' of the same tracking points 30 as represented in the initial model 51 of the tracking device. The sensed locations 66 of the remaining tracking points around the upper, lower, and lower left corners, however, correspond closely to the initial locations 53 of the corresponding tracking points 30. This deformation could be caused, for example, by excessive pressure against the nearby area of the skin of the patient near the upper right corner of the trackable device 26.

Figure 6:
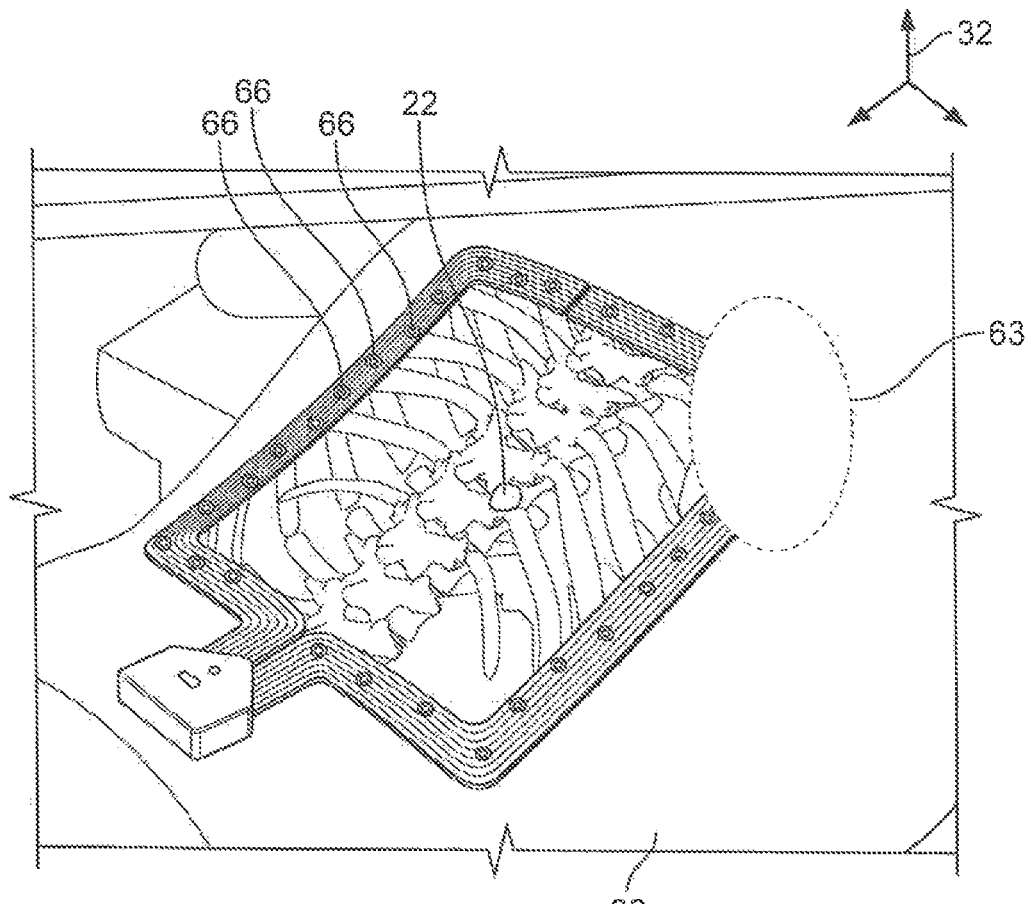
FIG. 6 is a schematic representation of a refined model of the trackable device in FIG. 1.

At a block 60, a refined model 62 of the trackable device 26 that compensates for the deformations sensed in block 58 is created, an example of which is shown schematically in FIG. 6. The refined model 62 is a model that based on a modification of the sensed locations of the tracking points after the initial model 51 has been registered to the image of the work target 22. The step of creating the refined model 62 may include excluding some tracking points that are deformed more than a selected deviation threshold from the initial shape of the trackable device 26 and/or may include adjusting a sensed location of a deformed tracking point relative to sensed locations of one or more of the other tracking points, as is explained in further detail hereinafter. In the example of FIG. 6, the refined model 62 is based on a set of the sensed locations of the tracking points that excludes the locations of tracking points that have been deformed beyond the deviation threshold. Thus, continuing with the example started above regarding FIG. 5, the refined model 62 in FIG. 6 excludes the tracking points of the upper right corner of the device, as shown schematically in the region 63 of the refined model 62 where no tracking points are shown. In this way, the refined model 62 is based on the sensed locations 66 of the tracking points 30 that have not been deformed excessively, while removing the excessively deformed tracking points from the refined model 62. This can improve the accuracy of the pose of the refined model 62 relative to the position of the work target 22 without necessitating interrupting the navigation procedure to re-register the trackable device 26 or otherwise re-set the entire setup.

Thereafter, a block 64 calculates the current position of the work target 22 from the refined model 68 in any suitable manner. Of course, it is understood that, if the sensed locations 66 of the tracking points 30 are not deformed beyond the acceptable limit, the navigation routine 36 may skip the block 60 and calculate the current position of the work target 22 directly from the model defined by the sensed locations 66 without performing further refinements to the model.

During a normal surgical navigation procedure, the blocks 50 and 56, and optionally the blocks 52 and 54, are normally performed a single time during a setup of the navigation procedure, and the blocks 58, 60, and 64 are normally iteratively repeated during the remaining course or some period of the navigation procedure until the navigation procedure is interrupted or ended for some reason. However, the iteration of the blocks 58, 60 and 64 is optional and may be performed only once and/or may include additional method steps interspersed therein.

The steps of sensing the deformations of the trackable device 26 and refining the model, as performed in the blocks 58 and 60 of the navigation routine 36 may be performed according to various different specific methods. In one exemplary method, the step of sensing deformations at block 58 includes tracking the subsequent locations 66 of the tracking points 30 after the initial model 51 has been registered to the initial location of the target 22 in the scan image. The subsequent locations 66 define a deformed model 68 having a deformed shape, which may be simply the shape of the point cloud defined by the sensed locations 66, as shown schematically in FIG. 5. Thereafter, the deformation of the trackable device 26 is identified based on one or more differences between the deformed shape 68 and the initial shape 51.

Figure 7:
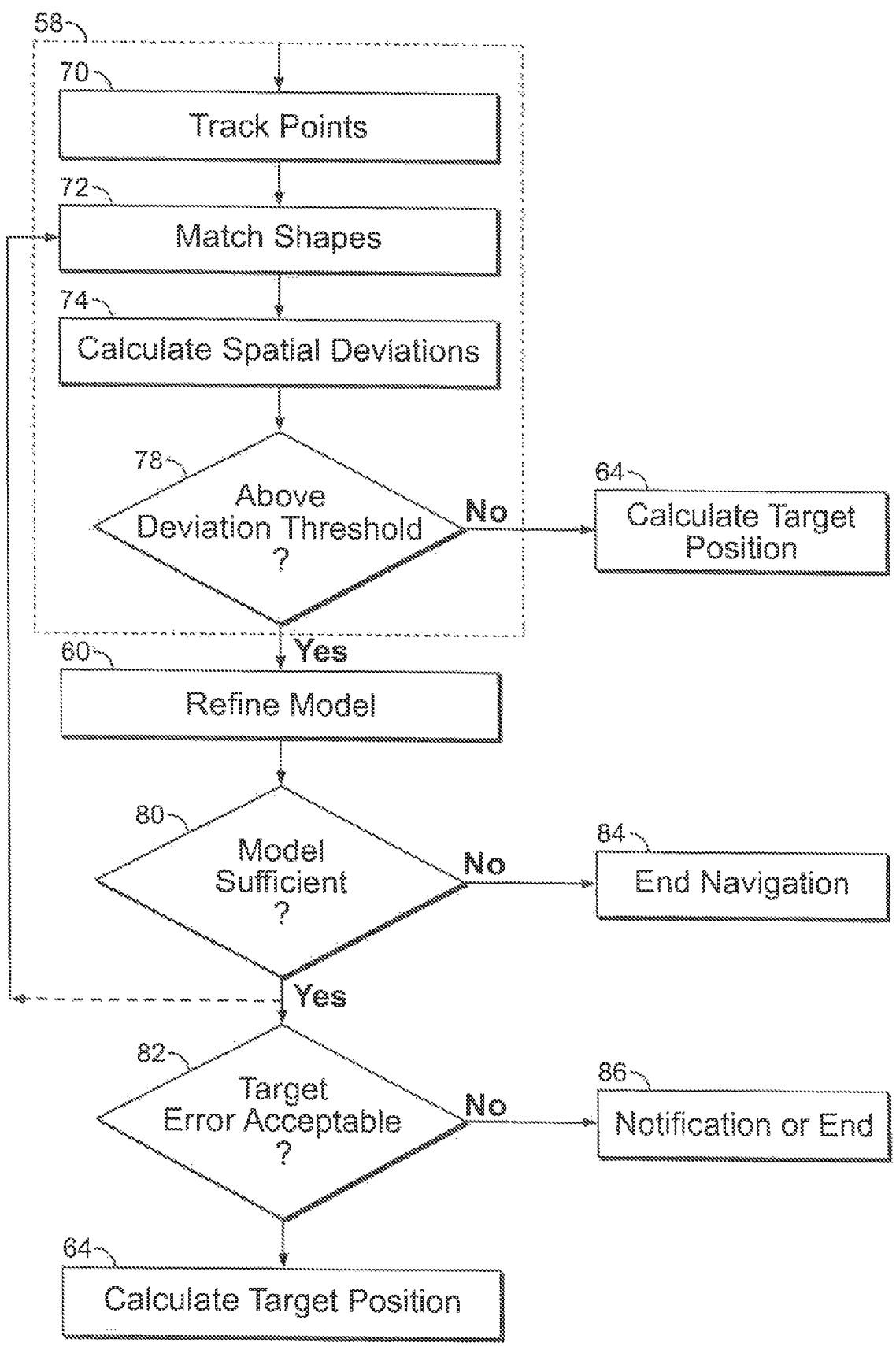
FIG. 7 is a logic flow diagram depicting some optional arrangements of the navigation routine of FIG. 2.

In the exemplary arrangement of FIG. 7, these steps are performed as part of the block 58. After the trackable device 26 has been registered to the work target 22 in the scan image, a block 70 obtains the subsequent location a set of the tracking points 30, for example with the sensors 38 of the tracking system 28. A block 72 identifies one or more deformations of the trackable device 26 based on one or more differences between the deformed shape 68 and the initial shape 51. With reference again to FIG. 5, in one method, the block 72 matches the initial shape 51 to the deformed shape 68. This matching may be performed by transforming the coordinates of the initial locations 55 of the tracking points 30 to the subsequent locations 66 of the tracking points 30 as sensed by the sensors 38. For example, the transformation may include an orthogonal transformation that is a result of a least squares match of the point cloud formed by the initial locations 55 with the point cloud formed by the subsequent locations 66. Alternatively, the coordinates of the subsequent locations could be transformed to match the coordinates of the initial locations, or both the initial and subsequent locations could be transformed to be based on a further coordinate system. The initial and deformed shapes 51 and 68 are matched by any suitable algorithm. One exemplary method includes performing a least squares analysis to find a best fit between the initial shape 51 and the deformed shape 68. However, other methods of matching the initial and deformed shapes may also be used.

After matching the best fit between the initial shape 51 and the deformed shape 68, a block 74 calculates a spatial deviation of one or more of the tracking points 30 of the set. As shown schematically in FIG. 5, the spatial deviation 76 may include the distance and/or direction between the subsequent location 66 of a particular tracking point and the transformed initial location 53 of the same tracking point. For example, the same tracking point 30 may have a coordinate 53' corresponding to the transformed initial location of the tracking point and a coordinate 66' corresponding to the subsequent location of the same tracking point. The spatial deviation 76' in this example is equal to absolute value of the distance between the coordinate 53' and the coordinate 66'. In some arrangement, the spatial deviation 76 may include both distance and direction between the coordinate 53' and the coordinate 66'. However, other methods of calculating the spatial deviation 76' may also be used. This calculation may be performed, such as iteratively, on all of the tracking points 30 in the set that define the deformed model 68 and/or can be performed on selected tracking points within the set.

A block 78 thereafter determines if one or more of the tracking points 30 is deformed (beyond an acceptable amount). In some arrangements, a tracking point 30 is considered to be deformed if it has a spatial deviation 76 that exceeds a selected deviation threshold and/or is larger than the spatial deviation of one or more of the other tracking points 30. The deviation threshold may be selected and/or defined as a static value and/or as a dynamic value. A static value may include an unchanging value, for example, a specific preselected distance above which the spatial deviation is considered to be too large and thereby considered an error. A dynamic value may change as a function of one or more selected parameters, for example, by being based on a comparison of the spatial deviation for a particular tracking point 30 in comparison to the spatial deviations of one or more other tracking points 30 in the set defining the models 52 and/or 68. However, other methods of selecting the deviation threshold may also be used. This determination may be performed individually on a point by point basis, such as by comparing each spatial deviation 76 with the deviation threshold, and/or or may be based on an agglomeration of a larger set of the tracking points, such as by comparing an averaged or composite spatial deviation of two or more of the tracking points 30 to the deviation threshold. In one exemplary arrangement, the spatial deviation of a particular tracking point 30 is compared with a pre-defined static deviation threshold. In addition, the difference of the spatial deviations of the tracking points with respect to each other is also considered. The tracking point 30 that exceeds a static pre-defined deviation threshold, for example about 2 mm, and that has the largest spatial deviation relative to the other tracking points is removed from the initial model. Then the iterative process starts with the refined model (less one tracking point) being matched with the initial model. Only one point, such as the worst tracking point (i.e., the tracking point with the largest spatial deviation), is excluded per iterative step. If there is still a second tracking point that both exceeds the deviation threshold and has the greatest deviation with respect to the other tracking points, then the iterative process repeats, and so on, until no further tracking points are removed from the model or the model does not have enough tracking points for suitable navigation. However, if all the remaining tracking points of the deformed model are not above the deviation threshold, then the target position is calculated. Similarly, if all the tracking points would have the same deviation value/vector above the deviation threshold, the model may not be altered because this deformation can be assumed to be a uniform movement of the patient 24 and/or trackable device 26 (e.g., translation of the entire patient) rather than a deformation of the trackable device 26. If one or more of the tracking points 30 has a spatial deviation greater than the deviation threshold and has the greatest spatial deviation of all the tracking points, then the navigation routine 36 advances to block 60 to refine the model before calculating the target position at block 64. Of course, if the tracking points of the deformed model 68 are not considered to be deformed, then the navigation routine 36 may optionally advance directly to block 64 to calculate the target position based on the deformed model itself.

In some arrangements, block 60 includes refining the model by removing, such as by excluding, one or more tracking points 30 from the refined model 62 when the tracking point has a spatial deviation above the deviation threshold. In this arrangement, the refined model 62 thereby has fewer tracking points than the initial model of the trackable device, as illustrated by way of example in FIG. 6. Thus, the refined model 62 is based on a reduced set of tracking points without the subsequent location of the removed tracking point. Optionally, the deformed tracking point is removed from the refined model 62 without modifying the shape of remaining portions of the deformed model 68. In another arrangement, the block 60 may refine the model by adjusting the subsequent location of one or more of the tracking points 30 without removing the tracking point from the set. In this arrangement, when the position 66' of a sensed tracking point is considered to be deformed, the location of the deformed tracking point in the deformed model 68 may be adjusted into a corrected position in the refined model. The sensed location of a tracking point may be adjusted relative to the sensed locations of the other tracking points in the set as a function of the relative positions of the tracking points to each other and the spatial deviations of these relative positions and/or relative distances. This adjustment may be performed based on a finite element method analysis, for example based on a force spring model assumption of movements of the skin of the patient 24. In this method, the spatial deviation 76' of a deformed tracking point 30 may be equated to a resultant force. A set of forces applied to the spring model may be calculated to shift the deformed tracking point back toward the original or initial position 53' in the initial model. The shift may result in the shifting of one or more of the remaining tracking points 30 in the refined model. However, other tracking points 30 in the refined model may be assumed to remain static relative to the position of the work target 22. In this way, the corrected position of the deformed tracking point may be retained in the refined model rather than omitted from the refined model. In addition, the block 60 may apply both of these methods of refining the model and/or other methods of refining the model so as to compensate for deformations of the tracking points 30 after the initial positions of the tracking points have been registered to the initial position of the work target 22 in the image data set.

After refining the model at block 60, the navigation routine 36 may optionally include one or more sufficiency checks such as at blocks 80 and 82 as shown in FIG. 7. The optional block 80 determines whether the refined model 62 is still sufficient for use in the navigation procedure. In one exemplary arrangement, if the step of refining the model includes removing one or more deformed tracking points from the refined model 62, the block 80 determines if the remaining set of tracking points in the refined model includes at least some predefined minimum number of tracking points that are considered to be acceptable for reasons of accuracy or otherwise. If not, then the refined model 62 is considered to be insufficient, and a block 84 provides a notification to a user that the model is no longer sufficient for navigation, such as by ending the navigation routine 36 and/or providing a warning signal. If the refined model 62 includes the minimum number of tracking points such that the model is considered sufficient, then the navigation routine may continue. In some arrangements, the steps of matching the initial and deformed shapes, calculating spatial deviations, and refining the model may be iteratively repeated after the block 80 until either no further tracking points are removed from the set of tracking points forming the refined model 62 or the refined model includes fewer than the predefined minimum number considered acceptable. Optionally, the block 80 may calculate an averaged spatial deviation of up to all of the tracking points in the set of tracking points defining the deformed model from the spatial deviations, and the navigation routine is ended at block 84 when the averaged spatial deviation exceeds a selected value.

Optional block 82 determines whether an estimated error in the calculated location of the work target will be within an acceptable error range. In one arrangement, this is performed by estimating an expected error of the calculated current position of the work target 22 based on the initial model 51 and the deformation of the trackable device 26. Such estimation may be performed according to any desired method and/or based on any desired set of parameters. If the estimated error in the calculated position of the work target is considered to be unacceptable, for example by exceeding a predefined maximum error threshold for the work target, block 86 provides a notification to the user, such as with a warning message, error message, and/or ending the navigation routine 36. If, however, the estimated error is considered to be acceptable, such as by being within the predefined maximum error threshold, block 64 then calculates the current position of the work target 22 based on the refined model 62.

Turning now to FIGS. 8 to 11, the trackable device 26, unlike trackable devices in many previous systems, does not need to have a rigid or even fixed shape, although a rigid or fixed shape trackable device 26 may be used with the tracking system 28 if desired. Rather, due to the capabilities of the navigation routine 36 to sense and compensate for deformations of the trackable device 26, it may be formed so as to allow one or more of the various tracking points 30 to shift, such as by deforming, relative to other ones of the tracking points 30 during a navigation procedure. Thus, any one of the following exemplary trackable devices 26*a*-*d* may be used as part of the navigation system 20.

Figure 8:
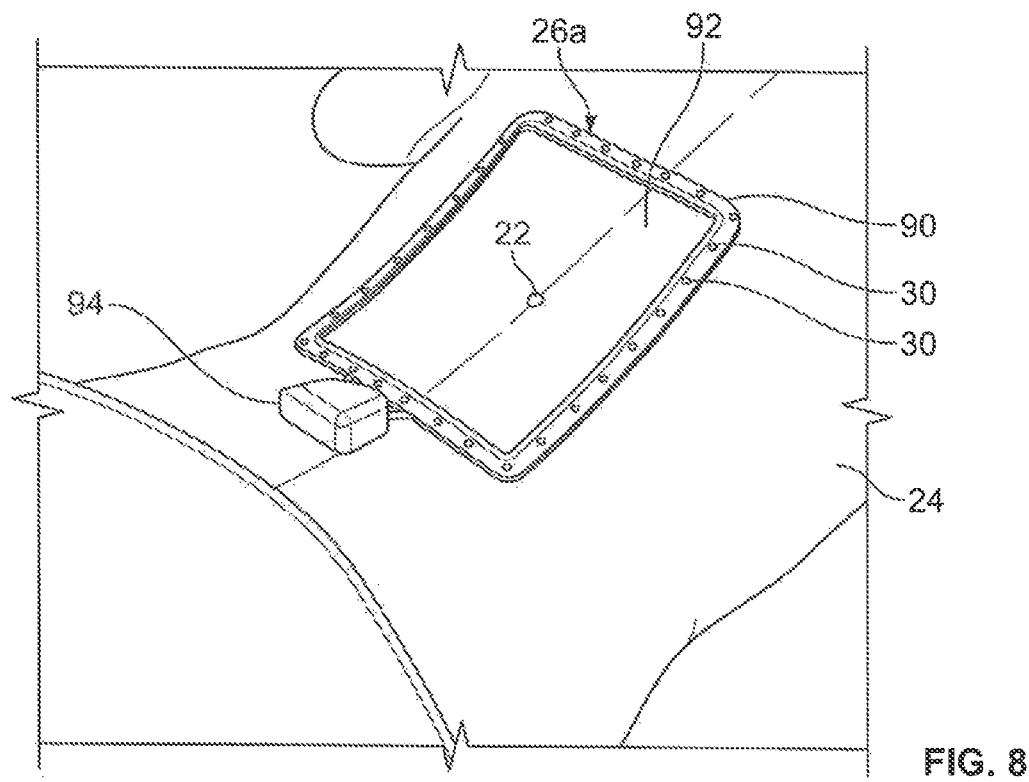
FIG. 8 is an isometric view of the exemplary trackable device shown in FIG. 1.

In FIG. 8, a trackable device 26*a* is secured to the skin of a patient 24. The trackable device 26*a* includes a flexible substrate 90 configured to be secure to the skin of the patient, for example with adhesive or straps. The flexible substrate 90 is in the form of a sheet having a relatively thin thickness that has unlimited flexibility, although in some arrangement it may have limited flexibility, such as by being flexible in only a limited number of directions. The tracking points 30 are carried by the flexible substrate 90. The tracking points 30 are in the form of optical tracking points, such as LEDs or passive optical marks that are visible to sensors 38 in the form of cameras. Although the following description refers to the use of LEDs for exemplary purposes, tracking systems that use passive visual markers may also be used with the systems and methods described herein. The tracking points 30 are disposed on one side of the substrate 90, and optionally an adhesive is disposed on the opposite side of the substrate for attaching the substrate 90 to the skin of the patient 24. The flexible substrate 90 is in the shape of a frame surrounding a central window 92 through a central portion of the trackable device 26*a*. The frame is shaped and sized such that the window 92 is large enough to encompass the area of the patient above the work target 22 and provide a surgeon with sufficient room to access the work target through the window 92 without excessively disturbing the shape of the frame. The frame is illustrated as being rectangular; however, other shapes are also possible.

The number of tracking points 30 carried by the flexible substrate 90 is preferably between 20 and 40 optical emitters disposed at regular intervals around the entire circumference of the frame. However, fewer or more tracking points 30 may be disposed on the flexible substrate 90 and may be grouped in different arrangements. The trackable device 26*a* optionally includes a data communication link 94 suitable for sending and/or receiving data to and/or from the tracking system 28. The data communication link 94 may include a wireless communication link, for example capable of communicating with the wireless communicator 48 of the computer processor 34. The data communication link 94 may include a hard-wired communication link, for example for connection with the cable 46 to the computer processor 34. Further optionally, the tracking points 30, if optical emitters such as LEDs, may be selectively activated in response to command signals received from the tracking system 28 through the data communication link 94. Also optionally, information regarding any physical constraints of how the tracking points 30 can move relative to each other may be communicated to the tracking system 28 with the data communication link 94. Such information may include information relative to the flexibility of the substrate 90, rigidity of the substrate 90, and/or the type of connection between tracking points 30 associated with the trackable device 26*a*. The information may be contained in one or more memory devices associated with the trackable device 26*a*, such as a non-volatile memory also carried with the substrate 90.

Figure 9:
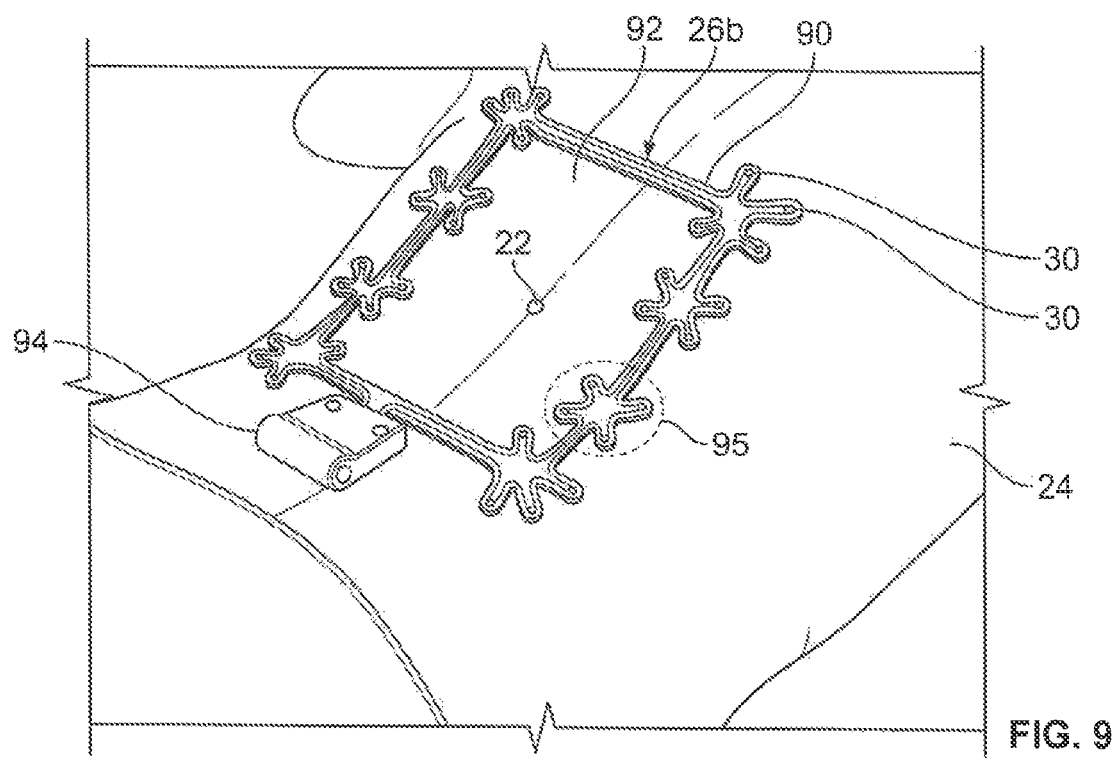
FIG. 9 is an isometric view of another exemplary trackable device usable in the navigation system of FIG. 1 according to additional aspects of the present disclosure.

FIG. 9 shows another form of a trackable device 26*b* suitable for use with the navigation system 20. Similar to the trackable device 26a, a plurality of tracking points 30, in the form of optical emitters such as LEDs, are disposed on one side of a flexible substrate 90 which is adapted to be secured to the skin of a patient with for example adhesive disposed on the opposite side of the flexible substrate. The trackable device 26b also includes a data communication link 94 and optionally a memory as described with regard to the trackable device 26a. The difference, is that the arrangement of the tracking points 30 is not necessarily in a square or rectangle as in FIG. 3. Rather, while the flexible substrate 90 forms generally the shape of a rectangular or square frame surrounding a central window 92, the tracking points 30 are arranged in clusters 95, here generally cross- or star-shaped clusters of four LEDs each, around the circumference of the frame shape of the flexible substrate 90. This may allow the individual clusters 95 of tracking points to be recognized individually as separate uniquely shaped tracking points 30 collectively. However, remaining portions of the trackable device 26b are substantially functionally the same as described with respect to the trackable device 26a.

Figure 10:
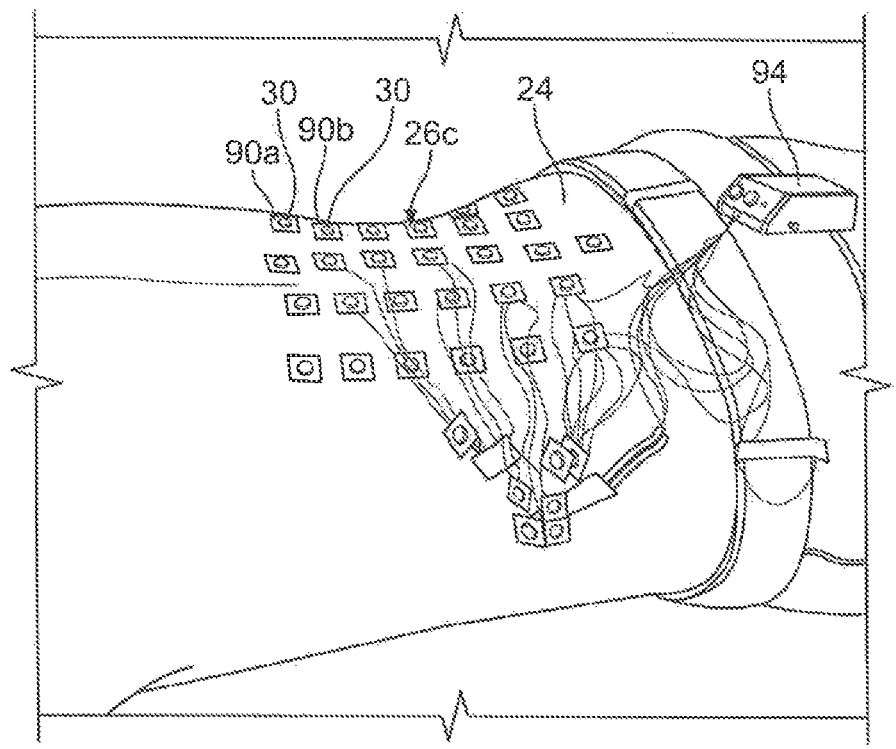
FIG. 10 is an isometric view of a further exemplary trackable device usable in the navigation system of FIG. 1 according to aspects of the present disclosure.

FIG. 10 shows another exemplary trackable device 26c including a number of different and separate substrates 90a, 90b, etc., for example in the form of patches. Each substrate 90a, 90b is configured to be secured to the outer surface of the patient spaced apart from the other substrates if desired. Each substrate 90a, 90b carries at least one of the tracking points 30. In some arrangements, one or more of the substrates 90a and 90b may carry multiple tracking points 30, for example, similar to the clusters 95 shown in the arrangement of FIG. 9. Although any number of separate substrates 90a, 90b may be used to form a trackable device 26c, preferably between 10 and 40 separate substrates are provided. In the exemplary form shown in FIG. 10, twenty four separate substrates 90a, 90b, etc. are attached to the skin of the patient 24. The trackable device 26c also includes a data communication link 94 and may also include a memory as described with regard to the trackable devices 26a and 26b. With the trackable device 26c, the substrates 90a, 90b may be selectively secured to the skin of the patient in almost any conceivable arrangement desired, such as in a grid as shown in the example of FIG. 5. In such a configuration, the trackable device 26c may use passive visual patches used in combination with a camera, such as a webcam, carried by the surgical instrument 40 to track the positions. Once secured to the skin of the patient 24, the trackable device 26c performs functionally similar or the same as the trackable devices 26a or 26b.

Figure 11:
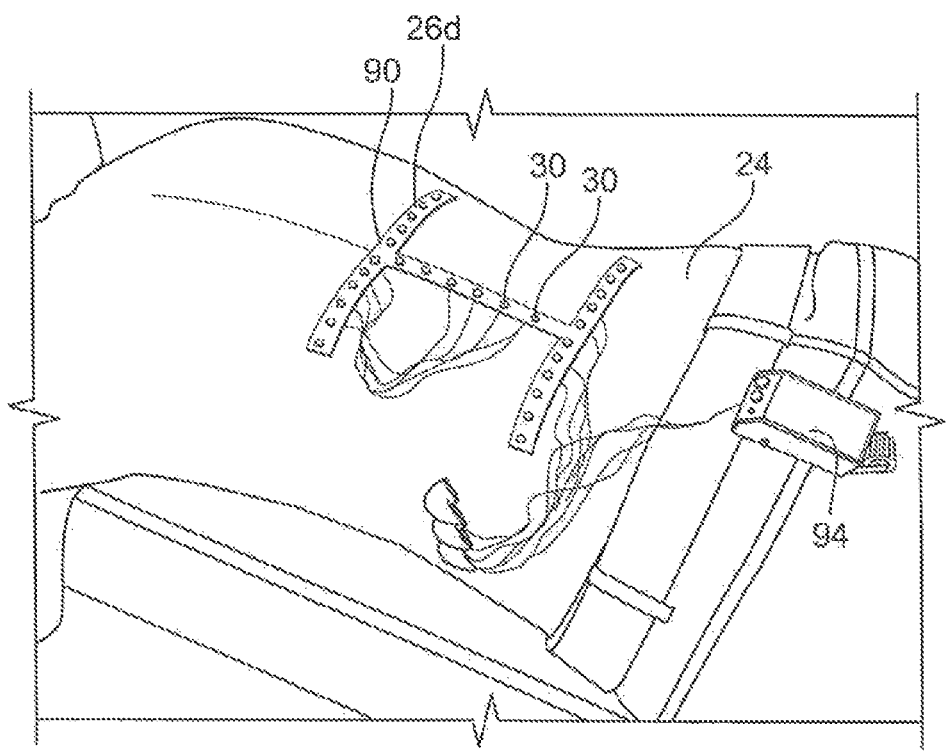
FIG. 11 is an isometric view of still a further exemplary trackable device usable in the navigation system of FIG. 1 according to aspects of the present disclosure.

FIG. 11 shows another exemplary trackable device 26d, in which the substrate 90 is shaped in the form of an H or I, and the tracking points 30 are spaced apart relatively evenly across the shape of the flexible substrate 90. The remaining portions of the trackable device 26d are functionally similar or identical to the corresponding components of the trackable devices 26a through 26c.

The tracking points 30 are selected to be sensed by the sensors 38 of the tracking system 28. Thus, depending on the type of sensor 38 used by the tracking system 28, the tracking points 30 may include LEDs, reflective surfaces, such as metal spheres, a reflective pattern, a magnetic coil, and/or an optically identifiable geometric shape that uniquely defines position and/or orientation of the tracking point 30. In some arrangements, at least one of the tracking points 30 may be an optical target that uniquely defines a unique pose, and the tracking system 28 includes a camera such as an optical video camera adapted to capture the image of the optical target. In this arrangement, the computer processor arrangement 34 is adapted to implement a tracking routine that calculates the pose of the optical target from the captured optical image of a single tracking point 30.

Next, an anticipated exemplary method of using the navigation system 20 is described when it is adapted for use as a surgical navigation system as shown schematically in FIG. 1. In a spinal procedure, for exemplary purposes, the trackable device 26 is secured to the skin of the patient 24 in the area of the work target 22, such as a specific target vertebrae. If the trackable device 26a is used, for example, the flexible substrate 90 is located to surround the target vertebrae so that the surgeon can gain access to the target vertebrae through the window 92. Thus, a mathematically strong distribution of tracking points 30 is provided around the work target 22 to provide a high accuracy, low error position calculation during the navigation procedure.

After the trackable device 26a is secured to the patient 24, it is registered to a preoperative image of the patient that includes an image of the target vertebrae. In one arrangement, the initial locations 53 of the tracking points 30 are gathered by the tracking system 28 with the sensors 38. Thereafter, the navigation routine 36 creates the initial model 51 from the initial locations 53, and registers the initial model 51 to the pre-operative scan image so that the actual position of the trackable device 26a is registered with the position of the actual target vertebrae and the image of the target vertebrae in the pre-operative scan image. Alternatively, a pre-operative image of the patient 24 with the trackable device 26a already attached may be obtained.

After registration is completed, the surgical procedure advances with the aid of the navigation system in a manner generally understood in the art. If the trackable device 26a is distorted during the navigated portion of the surgical procedure, the navigation system 20 can detect, and in some cases compensate for the distortions, so as to allow the surgical procedure to proceed without having to reset system, for example by having to re-register the trackable device 26a to the patient or the preoperative image.

In general, use of a non-rigid trackable device secured directly to the skin of the patient 24, such as the trackable device 26a, can improve accuracy of the navigation procedure by reducing the possibility of being bumped or sagging. The present navigation system improves on previous systems that used non-rigid trackable devices by being able to detect and, in some circumstances, compensate for potential distortions of the trackable device 26a during the navigated surgical procedure.

The features described in relation to the exemplary arrangements shown in the drawings can be readily combined to result in different embodiments, as suggested previously above. It is apparent, therefore, that the present disclosure may be varied in many ways. Such variations are not to be regarded as a departure from the scope of the invention, and all modifications within the scope of the appended claims are expressly included therein.

The invention claimed is:

1. A method for tracking movement of a patient during surgery comprising:
  acquiring image data by imaging the patient with a base layer of a skin-based patient tracking apparatus secured to the patient's skin with an adhesive material of an adhesive layer of the skin-based patient tracking apparatus, the skin-based patient tracking apparatus including a plurality of optical surgical tracking elements for use in continuously tracking movement of the patient's skin during surgery;
  registering patient position to the image data;

determining positions of the plurality of optical surgical tracking elements before a deformation of the skin-based patient tracking apparatus and positions of the plurality of optical surgical tracking elements after the deformation of the skin-based patient tracking apparatus;

determining an average position of the plurality of optical surgical tracking elements before the deformation of the skin-based patient tracking apparatus and an average position of the plurality of optical surgical tracking elements after the deformation of the skin-based patient tracking apparatus based on the determined positions of the plurality of optical surgical tracking elements before the deformation of the skin-based patient tracking apparatus and the determined positions of the plurality of optical surgical tracking elements after the deformation of the skin-based patient tracking apparatus; and tracking the movement of the patient's skin by determining a deviation between the average position of the plurality of optical surgical tracking elements before the deformation of the skin-based patient tracking apparatus and the average position of the plurality of optical surgical tracking elements after the deformation of the skin-based patient tracking apparatus, wherein the adhesive material sticks the skin-based patient tracking apparatus to the patient's skin such that the movement of the patient's skin results in corresponding movement of the plurality of optical surgical tracking elements to provide the skin-based patient tracking apparatus as a dynamic reference frame for use in continuously tracking the movement of the patient's skin during surgery.

2. The method of claim 1, wherein the movement of the patient's skin is tracked when an incision in the patient's skin is made at a surgical area, wherein the incision results in the deformation of the skin-based patient tracking apparatus.

3. The method of claim 1, wherein the skin-based patient tracking apparatus is configured such that the plurality of optical surgical tracking elements are located on the patient's skin in an area around a surgical area.

4. The method of claim 1, wherein the patient position has a fixed spatial relationship to a work target.

5. The method of claim 4, wherein the skin-based patient tracking apparatus is configured such that the plurality of optical surgical tracking elements are located on the patient's skin in an area around the work target.

6. The method of claim 4, wherein the work target is at least one of a bone, an organ, the spine, a lung, the liver, a femur, the pelvis and an item disposed in, on or near the patient's body.

7. A navigation system for tracking movement of a patient during surgery comprising:
   image acquisition means configured to acquire image data by imaging the patient with a base layer of a skin-based patient tracking apparatus secured to the patient's skin with an adhesive material of an adhesive layer of the skin-based patient tracking apparatus, the skin-based patient tracking apparatus including a plurality of optical surgical tracking elements for use in continuously tracking movement of the patient's skin during surgery; and
   a computer processor arrangement adapted to implement a navigation routine that includes the steps:
      registering patient position to the image data;
      determining a spatial deviation for each of the plurality of optical surgical tracking elements to generate a plurality of spatial deviations, the spatial deviation for each of the plurality of optical surgical tracking elements being a deviation between a position of the optical surgical tracking element before a deformation of the skin-based patient tracking apparatus and a position of the optical surgical tracking element after the deformation of the skin-based patient tracking apparatus; and
      tracking the movement of the patient's skin by determining an average of the plurality of spatial deviations,
   wherein the adhesive material is configured to stick the skin-based patient tracking apparatus to the patient's skin such that the movement of the patient's skin results in corresponding movement of the plurality of optical surgical tracking elements to provide the skin-based patient tracking apparatus as a dynamic reference frame for use in continuously tracking the movement of the patient's skin during surgery.

8. The system of claim 7, wherein the movement of the patient's skin is tracked when an incision in the patient's skin is made at a surgical area, wherein the incision results in the deformation of the skin-based patient tracking apparatus.

9. The system of claim 7, wherein the skin-based patient tracking apparatus is configured such that the plurality of optical surgical tracking elements are located on the patient's skin in an area around a surgical area.

10. The system of claim 7, wherein the patient position has a fixed spatial relationship to a work target.

11. The system of claim 10, wherein the skin-based patient tracking apparatus is configured such that the plurality of optical surgical tracking elements are located on the patient's skin in an area around the work target.

12. The system of claim 10, wherein the work target is at least one of a bone, an organ, the spine, a lung, the liver, a femur, the pelvis and an item disposed in, on or near the patient's body.

13. The system of claim 7, further comprising the skin-based patient tracking apparatus.

14. The system of claim 7, wherein the image acquisition means comprises at least one camera.

15. The system of claim 7, wherein tracking the movement of the patient's skin comprises:
   comparing the determined spatial deviation of at least one of the plurality of optical surgical tracking elements to the average of the plurality of spatial deviations; and
   tracking the movement of the patient's skin based on the comparison.

16. The system of claim 7, wherein tracking the movement of the patient's skin comprises:
   comparing the average of the plurality of spatial deviations to a deviation threshold; and
   tracking the movement of the patient's skin based on the comparison.

17. A navigation system for tracking movement of a patient during surgery comprising:
   a scanner configured to acquire scan data by scanning the patient with a base layer of a skin-based patient tracking apparatus secured to the patient's skin with an adhesive material of an adhesive layer of the skin-based patient tracking apparatus, the skin-based patient tracking apparatus including a plurality of optical surgical tracking elements for use in continuously tracking movement of the patient's skin during surgery; and a computer processor arrangement adapted to implement a navigation routine that includes the steps:
registering patient position to the scan data;
determining positions of the plurality of optical surgical tracking elements before a deformation of the skin-based patient tracking apparatus and positions of the plurality of optical surgical tracking elements after the deformation of the skin-based patient tracking apparatus;
determining an average position of the plurality of optical surgical tracking elements before the deformation of the skin-based patient tracking apparatus and an average position of the plurality of optical surgical tracking elements after the deformation of the skin-based patient tracking apparatus based on the determined positions of the plurality of optical surgical tracking elements before the deformation of the skin-based patient tracking apparatus and the determined positions of the plurality of optical surgical tracking elements after the deformation of the skin-based patient tracking apparatus; and
tracking the movement of the patient's skin by determining a deviation between the average position of the plurality of optical surgical tracking elements before the deformation of the skin-based patient tracking apparatus and the average position of the plurality of optical surgical tracking elements after the deformation of the skin-based patient tracking apparatus,
wherein the adhesive material is configured to stick the skin-based patient tracking apparatus to the patient's skin such that the movement of the patient's skin results in corresponding movement of the plurality of optical surgical tracking elements to provide the skin-based patient tracking apparatus as a dynamic reference frame for use in continuously tracking the movement of the patient's skin during surgery.

18. The system of claim 17, further comprising the skin-based patient tracking apparatus.

19. The system of claim 17, wherein the movement of the patient's skin is tracked when an incision in the patient's skin is made at a surgical area, wherein the incision results in the deformation of the skin-based patient tracking apparatus.

20. The system of claim 17, wherein the skin-based patient tracking apparatus is configured such that the plurality of optical surgical tracking elements are located on the patient's skin in an area around a surgical area.

* * * * *